(12) United States Patent
Baran, Jr. et al.

(10) Patent No.: US 7,109,247 B2
(45) Date of Patent: Sep. 19, 2006

(54) STABILIZED PARTICLE DISPERSIONS CONTAINING NANOPARTICLES

(75) Inventors: Jimmie R. Baran, Jr., Prescott, WI (US); James S. Stefely, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 190 days.

(21) Appl. No.: 10/449,677

(22) Filed: May 30, 2003

(65) Prior Publication Data

US 2004/0242730 A1 Dec. 2, 2004

(51) Int. Cl.
*A61K 8/00* (2006.01)
*B01F 3/08* (2006.01)
*B01F 3/12* (2006.01)

(52) U.S. Cl. .................. 516/31; 516/22; 424/401; 514/844; 514/938

(58) Field of Classification Search ................ 516/31
See application file for complete search history.

(56) References Cited

U.S. PATENT DOCUMENTS

| | | | |
|---|---|---|---|
| 2,801,185 A | 7/1957 | Iler | |
| 4,522,958 A | 6/1985 | Das et al. | |
| 4,680,173 A | 7/1987 | Burger | |
| 5,145,684 A | 9/1992 | Liversidge et al. | |
| 5,262,150 A | 11/1993 | Laugier et al. | |
| 5,492,688 A | 2/1996 | Byron et al. | |
| 5,612,021 A * | 3/1997 | Mellul | 424/61 |
| 5,672,662 A | 9/1997 | Harris et al. | |
| 5,695,747 A | 12/1997 | Forestier et al. | |
| 5,858,330 A | 1/1999 | Boltri et al. | |
| 6,001,342 A * | 12/1999 | Forestier et al. | 424/76.1 |
| 6,004,567 A * | 12/1999 | Marchi-Lemann et al. | 424/401 |
| 6,020,419 A * | 2/2000 | Bock et al. | 524/590 |
| 6,245,319 B1 | 6/2001 | Quay | |
| 6,258,896 B1 * | 7/2001 | Abuelyaman et al. | 525/437 |
| 6,309,623 B1 | 10/2001 | Weers et al. | |
| 6,319,513 B1 | 11/2001 | Dobrozsi | |
| 6,586,483 B1 | 7/2003 | Kolb et al. | |
| 6,811,767 B1 | 11/2004 | Bosch et al. | |
| 6,844,429 B1 * | 1/2005 | Mikata et al. | 536/1.11 |
| 2001/0046474 A1 | 11/2001 | Weers et al. | |
| 2002/0037316 A1 | 3/2002 | Weers et al. | |
| 2004/0081627 A1 * | 4/2004 | Jinks et al. | 424/46 |
| 2004/0127580 A1 * | 7/2004 | Baran, Jr. | 516/22 |
| 2004/0127612 A1 * | 7/2004 | Baran et al. | 524/236 |

FOREIGN PATENT DOCUMENTS

| | | | |
|---|---|---|---|
| DE | 837 243 | | 4/1952 |
| FR | 2 830 450 A1 | | 4/2003 |
| WO | WO 01/85324 | * | 11/2001 |
| WO | WO 02/30394 A2 | | 4/2002 |
| WO | WO 02/053659 A2 | | 7/2002 |
| WO | WO 02/057285 | * | 7/2002 |

OTHER PUBLICATIONS

U.S. Appl. No. 10/335,290, filed Dec. 31, 2002, Emulsion Including Surface-Modified Inorganic Nanoparticles.
U.S. Appl. No. 10/334,963, filed Dec. 31, 2002, Stabilized Foams Including Surface-Modified Organic Molecules.
U.S. Appl. No. 10/335,495, filed Dec. 31, 2002, Emulsions Including Surface-Modified Organic Molecules.
U.S. Appl. No. 10/449,359, filed May 30, 2003, Stabilized Particle Dispersions Containing Surface-Modified Inorganic Nanoparticles.
U.S. Appl. No. 10/449,443, filed May 30, 2003, Stabilized Aerosol Dispersions.
Alargova et al., "Stable Colloidal Dispersions of Fullerenes in Polar Organic Solvents", J. Am. Chem. Soc., 2001, vol. 123, pp. 10460-10467.
Kibbe Ah et ., *Handbook of Pharmaceutical Excipients*, 3$^{rd}$ Ed., 2000, "Colloidal Silicon Dioxide", pp. 143-145.

* cited by examiner

*Primary Examiner*—Randy Gulakowski
*Assistant Examiner*—Timothy J. Kugel

(57) ABSTRACT

In one aspect, the invention provides a stable dispersion comprising a continuous phase comprising a continuous liquid phase and a plurality of organic nanoparticles; and a dispersed phase comprising particles dispersed in the continuous phase.

24 Claims, No Drawings

STABILIZED PARTICLE DISPERSIONS CONTAINING NANOPARTICLES

BACKGROUND

Traditional dispersions are made up of two phases: a dispersed phase and a continuous phase. The most common dispersions consist of dispersed particles and a liquid continuous phase. If the formed dispersion is not stabilized, the dispersed particles tend to flocculate or agglomerate and the two phases will separate. Typically, dispersants are used to prevent the two phases from completely separating. Dispersants stabilize dispersions after being adsorbed onto the dispersed particles. Increasing the viscosity of the continuous phase may also prevent complete phase separation of dispersions.

SUMMARY

In one aspect, the invention provides a stable dispersion comprising a continuous phase comprising a continuous liquid phase and organic nanoparticles; and a dispersed phase comprising particles dispersed in the continuous phase.

In another aspect, the invention provides a method of stabilizing a dispersion comprising adding an effective amount of organic nanoparticles to a dispersion comprising a dispersed solid phase and a liquid continuous phase.

In another aspect, the invention provides a method for treating a mammal comprising administering a therapeutically effective amount of a medicament dispersion according to the invention to the mammal by administration methods selected from the group consisting of orally, injection, topically, through its nasal passage, by inhalation, and combinations thereof.

In another aspect, the invention provides a dispersion kit comprising a dispersed phase component to be dispersed in a continuous phase, and organic nanoparticles.

DETAILED DESCRIPTION

The dispersions of the invention are stable dispersions that remain dispersed over a useful time period without substantial agitation of the dispersion or which are easily redispersed with minimal energy input. The dispersions comprising dispersed particles and a continuous phase are rendered stable by incorporation of an effective amount of organic nanoparticles into the continuous phase. An "effective amount" of organic nanoparticles is an amount that minimizes the aggregation of the dispersed particles and forms stable dispersions that remain dispersed over a useful time period without substantial agitation of the dispersion or which are easily redispersed with minimal energy input. Without wishing to be bound by any theory, the nanoparticles are believed to sterically inhibit the aggregation of the dispersed particles and not through particle charge. The nanoparticles used in the dispersions of the invention appear to be soluble in the continuous phase of the dispersion and do not precipitate, flocculate, etc., in the dispersions of the invention. In addition, the nanoparticles do not substantially associate with the surface of the dispersed particles and may be effective suspension aids at low concentrations as compared with conventional suspension aids. The stable dispersions of the invention may contain less than 0.001 weight percent of surfactant, surface-active agents, traditional emulsifiers, detergents, and/or protective colloids.

As used herein, "dispersion" means a solid distributed throughout a liquid continuous phase which does not separate over a useful time period.

As used herein, "separate" means that the solid particles in a liquid dispersion gradually settle or cream, forming distinct layers with very different concentrations of the solid particles and continuous liquid phase.

As used herein, "dispersion stability" is a description of the tendency of a dispersion to separate. For a dispersion with good dispersion stability, the particles remain approximately homogeneously distributed within the continuous phase. For a dispersion with poor dispersion stability, the particles do not remain approximately homogeneously distributed within the continuous phase and may separate.

As used herein, an "excipient" refers broadly to any inert additive other than the primary active medicament moiety used to improve some aspect of the aerosol dispersion formulation.

As used herein, "nanoparticles" means organic particles or molecules that appear to be soluble in the continuous phase wherein each organic particle has nanoscale dimensions in the continuous phase and that occupies or provides a zone of steric exclusion of less than 100 nanometers, within the continuous phase.

Stabilized dispersions of the invention include surface-modified organic nanoparticles, and/or steric organic molecules having un-modified surfaces (nanoparticles). "Steric organic molecules" means single molecules (for example, polymers) that have an exclusion volume describable in nanometer diameter dimensions and comprised of covalently-bound organic units. "Steric organic molecules" do not include linear polymers that are soluble in the continuous phase. In one embodiment, they are substantially composed of the same moieties on the surface as are present in the inner portion or core of the nanoparticle. The nanoparticles are desirably individual, unassociated (i.e., non-aggregated) nanoparticles dispersed throughout the continuous phase and desirably do not irreversibly associate with each other and do not associate with the dispersed medicament. The term "associate with" or "associating with" includes, for example, covalent bonding, hydrogen bonding, electrostatic attraction, London forces, and hydrophobic interactions.

The nanoparticles are selected such that the composition formed therewith is free from a degree of particle agglomeration or aggregation that would interfere with the desired properties of the composition. The surface-modified organic nanoparticles have surface groups that modify the "solubility" or "wettability" characteristics of the nanoparticles. The surface groups are selected to render the particle compatible with the continuous phase including components of the continuous phase. The un-modified nanoparticles are compatible with the continuous phase without further surface modification.

One method of assessing the compatibility of the organic nanoparticles with the liquid continuous phase includes determining whether the resulting composition separates. For transparent liquid continuous phases, one useful method of assessing the compatibility of the organic nanoparticles with the transparent liquid continuous phase includes the step of combining the organic nanoparticles and the liquid continuous phase and observing whether the organic nanoparticles completely disperse in the liquid continuous phase. Since the nanoparticles have dimensions smaller than the wavelength of visible light, complete dispersion will result in a transparent dispersion.

When the nanoparticles are smaller than the wavelength of visible light, the nanoparticles will appear to form a transparent solution when completely dispersed. As the size of the organic nanoparticles increases, the haziness of the continuous phase generally increases. Desirable organic nanoparticles are selected such that they do not settle out of the continuous phase.

A further step in assessing the compatibility of the continuous phase and the organic nanoparticles includes determining whether, upon subsequent introduction of liquid to be dispersed in the continuous phase, the composition forms a stable dispersion phase in a useful period of time. A useful period of time may be minutes, hours, days, weeks, or years, depending upon the application. For example, when the dispersion of the invention is a pigment, it is desirable for the dispersion to remain stable for months. However, if the dispersion of the invention is a pharmaceutical formulation, it may only be necessary for the dispersion to remain stable for several minutes, until the pharmaceutical is administered.

Examples of suitable organic nanoparticles include buckminsterfullerenes (fullerenes), dendrimers, organic polymeric nanospheres, insoluble sugars such as lactose, trehalose, glucose or sucrose; aminoacids, and linear or branched or hyperbranched "star" polymers such as 4, 6, or 8 armed polyethylene oxide (available, for example, from Aldrich Chemical Company or Shearwater Corporation, Huntsville, Ala.) with a variety of end groups, and combinations thereof, and include combined materials such as a mixture of materials or layers of materials surrounding a central organic core.

Specific examples of fullerenes include $C_{60}$, $C_{70}$, $C_{82}$, and $C_{84}$. Specific examples of dendrimers include polyamidoamine (PAMAM) dendrimers of Generations 2 through 10 (G2–10), available from, for example, Aldrich Chemical Company, Milwaukee, Wis.

Specific examples of a useful organic polymeric nanospheres include nanospheres that comprise polystyrene, available from Bangs Laboratories, Inc., Fishers, Ind., as powders or dispersions. Average particle sizes of the polystyrene nanospheres range from at least 20 nm to not more than 60 nm. Current commercially available average particle sizes are 20, 30, 50, and 60 nm.

As one skilled in the art will understand, the nanoparticles described above may be used as is or surface-modified and in combination. Insoluble nanoparticles (such as sugars, such as trehalose or lactose, or certain dendrimers) should be appropriately surface modified to make them wettable in the continuous phase. The modification may also be used to control the volume of the zone of steric exclusion. Non-limiting methods for surface modification include adsorption, ionic, or covalent chemical reaction with the "surface", or encapsulating or coating the nanoparticle with a reactive moiety to create a shell that increases the "solubility" of the particle in the continuous phase. If adsorption is the primary method of modifying the surface of the nanoparticle, the adsorbed species should be selected by one skilled in the art so to avoid substantial desorption and subsequent modification of the surface of the medicament.

For surface-modified organic nanoparticles, the nature of the organic particle component of the surface-modified nanoparticle will prevent the surface-modified particle from actually dissolving in the continuous phase, i.e., the surface-modified nanoparticles will be dispersed in the continuous phase. However, the compatibility of the surface groups with the continuous phase will give the surface-modified nanoparticles the appearance of dissolving in the continuous phase.

Suitable surface groups can also be selected based upon the solubility parameter of the surface group and the continuous phase. Desirably the surface group, or the agent from which the surface group is derived, has a solubility parameter similar to the solubility parameter of the continuous phase. When the continuous phase is hydrophobic, for example, one skilled in the art can select from among various hydrophobic surface groups to achieve a surface-modified particle that is compatible with the hydrophobic continuous phase. Similarly, when the continuous phase is hydrophilic, one skilled in the art can select from hydrophilic surface groups, and, when the continuous phase is a hydrofluorocarbon, one skilled in the art can select from among various compatible surface groups. The nanoparticle can also include at least two different surface groups that combine to provide an organic nanoparticle having a solubility parameter that is similar to the solubility parameter of the continuous phase. The surface-modified organic nanoparticles are not amphiphilic.

The surface groups may be selected to provide a statistically averaged, randomly surface-modified particle.

If required, the surface groups are present on the surface of the nanoparticle in an amount sufficient to provide surface-modified organic nanoparticles that are capable of being subsequently dispersed in the continuous phase without aggregation. The surface groups desirably are present in an amount sufficient to form a monolayer, desirably a continuous monolayer, on the surface of the nanoparticle.

Surface modifying groups may be derived from surface modifying agents. Schematically, surface modifying agents can be represented by the formula A-B, where the A group is capable of attaching to the surface of the particle and the B group is a compatibilizing group (non-reactive with the continuous phase) or a linking group to a compatibilizing group. Compatibilizing groups can be selected to render the particle relatively more polar, relatively less polar, or relatively non-polar.

PAMAM dendrimers are currently commercially available with primary amine, hydroxyl, carboxylate sodium salt, mixed amine/hydroxyl, and $C_{12}$ surface functional groups. One skilled in the art will recognize these dendrimers can be used as is or modified to make the surface compatible with the continuous phase if required.

Useful surface-modifying groups for fullerenes and PAMAM dendrimers include straight or branched alkyl groups and may range from at least $C_3$ to not greater than $C_{30}$ and may be any size or range in between $C_3$ and $C_{30}$.

Useful organic acid surface-modifying agents include, e.g., oxyacids of carbon (e.g., carboxylic acid), sulfur and phosphorus, and combinations thereof.

Representative examples of polar surface-modifying agents having carboxylic acid functionality include $CH_3O(CH_2CH_2O)_2CH_2COOH$ (hereafter MEEAA) and 2-(2-methoxyethoxy)acetic acid having the chemical structure $CH_3OCH_2CH_2OCH_2COOH$ (hereafter MEAA), acid functionalized polyethylene glycols (PEGS), such as mono(polyethylene glycol) succinate and polyethylene glycols mono substituted with acetic, propionic, or butanoic acids. Such polymers or their derivatives may be prepared for example, as described in U.S. Pat. No. 5,672,662, incorporated herein, or purchased commercially.

Representative examples of non-polar surface-modifying agents having carboxylic acid functionality include octanoic acid, dodecanoic acid, and oleic acid.

Examples of suitable phosphorus containing acids include phosphonic acids including, e.g., octylphosphonic acid, laurylphosphonic acid, decylphosphonic acid, dodecylphosphonic acid, octadecylphosphonic acid, and phosphate or phosphonic substituted polyethylene glycols.

Useful organic base surface-modifying agents include, e.g., alkylamines including, e.g., octylamine, decylamine, dodecylamine and octadecylamine, or amine functionalized polyethylene glycols.

Examples of other useful surface modifying agents include acrylic acid, methacrylic acid, beta-carboxyethyl acrylate, mono-2-(methacryloyloxyethyl)succinate, and combinations thereof. A useful surface modifying agent that imparts both polar character and reactivity to the nanoparticles is mono(methacryloyloxypolyethyleneglycol)succinate.

Examples of suitable surface-modifying alcohols include, e.g., aliphatic alcohols including, e.g., octadecyl, dodecyl, lauryl and furfuryl alcohol, alicyclic alcohols including, e.g., cyclohexanol, and aromatic alcohols including, e.g., phenol and benzyl alcohol, polyethylene glycols, monomethyl polyethylene glycols, and combinations thereof.

A variety of methods are available for modifying the surface of nanoparticles including, e.g., adding a surface modifying agent to nanoparticles (e.g., in the form of a powder or a colloidal dispersion) and allowing the surface modifying agent to react with the nanoparticles. One skilled in the art will recognize that multiple synthetic sequences to bring the nanoparticle together with the compatibilizing group are possible and are envisioned within the scope, e.g., the reactive group/linker may be reacted with the nanoparticle followed by reaction with the compatibilizing group. Alternatively, the reactive group/linker may be reacted with the compatibilizing group followed by reaction with the nanoparticle. Other useful surface modification processes are described in, e.g., U.S. Pat. Nos. 2,801,185 and 4,522,958, and incorporated herein.

The nanoparticles, whether surface-modified, or not, have an average particle diameter less than about 100 nm; in other embodiments, no greater than about 50, 40, 30, 20, 15, 10, or 5 nm; in other embodiments, from about 3 nm to about 50 nm; in other embodiments, from about 3 nm to about 20 nm; and in other embodiments, from about 5 nm to about 10 nm. If the nanoparticles are aggregated, the maximum cross-sectional dimension of the aggregated particle is within any of these preferable ranges.

The nanoparticles are employed in the dispersions of the invention in an effective amount to minimize aggregation of the dispersed particles. Organic nanoparticles are generally present in an amount from 0.005 to 0.5 percent by weight and may be present in any amount or range between 0.005 and 0.5 percent by weight. In other embodiments, the dispersions of the invention contain less than 0.5, 0.4, 0.3, or 0.2 percent by weight. One skilled in the art will recognize that the effective amount required will depend upon the type of continuous phases, the surface functionality and particle size of the nanoparticles, the dispersed particle concentration and type, and the presence of other excipients.

The stabilized dispersions of the invention have a liquid continuous phase. The continuous phase may be made up of one or more miscible or soluble constituents so long as the dispersed particles may be dispersed in all of the constituents of the continuous phase.

Example liquid continuous phases include water, organic liquids including, e.g., acids, alcohols, ketones, aldehydes, amines, amides, esters, glycols, ethers, hydrocarbons, halocarbons, monomers, oligomers, lubricating oils, vegetables oils (including mono- di, and tri-glycerides), silicone oils, moisturizing oils (for example, mineral and jojoba oils), fuel oils, fuels (including kerosene, gasoline, diesel fuel), oligomers of ethylene glycol, alkyl and aryl nitro compounds, partially or fully fluorinated compounds, and polymers and combinations thereof. In some embodiments, the liquid continuous dispersions may be at least 95, 90, 85, 80, 75, 70, 65, 60, 55, 50, 45, 40, 35, 30, 25, 20, 15, 10, 5 weight percent water and may be any range between 100 and 0 weight percent water. In some embodiments, the liquid continuous dispersions may be at least 95, 90, 85, 80, 75, 70, 65, 60, 55, 50, 45, 40, 35, 30, 25, 20, 15, 10, 5 weight percent organic and may be any range between 100 and 0 weight percent organic.

The continuous phase may have additional components dissolved in it that do not affect the stability of the dispersion (aid or hinder the dispersion of the dispersed insoluble particles), for example, excipients that affect the biologic suitability, salts or organic materials, or other beneficial properties of the dispersion.

The dispersed phase may be any particle of interest that have minimal solubility in the liquid continuous phase. Desirably, the particles have a maximum diameter of less than about 100 micrometers. The dispersed particles may be inorganic, organic, or a combination thereof. Examples of dispersed particles include medicaments, carbon black, titanium dioxide, exfolients, cosmetics, pigments, and abrasives.

Specific medicaments include antiallergics, analgesics, bronchodilators, antihistamines, therapeutic proteins and peptides, antitussives, anginal preparations, antibiotics, anti-inflammatory preparations, diuretics, hormones, or sulfonamides, such as, for example, a vasoconstrictive amine, an enzyme, an alkaloid or a steroid, and combinations of these specific examples or medicaments which may be employed are: isoproterenol, phenylephrine, phenylpropanolamine, glucagon, adrenochrome, trypsin, epinephrine, ephedrine, narcotine, codeine, atropine, heparin, morphine, dihydromorphinone, dihydromorphine, ergotamine, scopolamine, methapyrilene, cyanocobalamin, terbutaline, rimiterol, salbutamol, isoprenaline, fenoterol, oxitropium bromide, reproterol, budesonide, flunisolide, ciclesonide, formoterol, fluticasone propionate, salmeterol, procaterol, ipratropium, triamcinolone acetonide, tipredane, mometasone furoate, colchicine, pirbuterol, beclomethasone, beclomethasone dipropionate, orciprenaline, fentanyl, diamorphine, and dilitiazem. Others are antibiotics, such as neomycin, cephalosporins, streptomycin, penicillin, procaine penicillin, tetracycline, chlorotetracycline and hydroxytetracycline; adrenocorticotropic hormone and adrenocortical hormones, such as cortisone, hydrocortisone, hydrocortisone acetate and prednisolone; antiallergy compounds such as cromolyn sodium, nedocromil protein and peptide molecules such as insulin, pentamidine, calcitonin, amiloride, interferon, LHRH analogues, IDNAase, heparin, etc. If applicable, the medicaments exemplified above may be used as either the free base or as one or more salts known to the art. Vaccines may also benefit from this approach.

The medicaments exemplified above may be used as either the free base or as one or more salts known to the art. The choice of free base or salt will be influenced by the physical stability of the medicament in the formulation. For example, it has been shown that the free base of salbutamol exhibits a greater dispersion stability than salbutamol sulphate in the formulations of the invention.

The following salts of the medicaments mentioned above may be used: acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate (embonate), pantothenate, phosphate-diphosphate, polygalacturonate, salicylate, stearate, subacetate, succinate, sulphate, tannate, tartrate, and triethiodide.

Cationic salts may also be used. Suitable cationic salts include the alkali metals, e.g., sodium and potassium, and ammonium salts and salts of amines known in the art to be pharmaceutically acceptable, e.g., glycine, ethylene diamine, choline, diethanolamine, triethanolamine, octadecylamine, diethylamine, triethylamine, 1-amino-2-propanol-amino-2-(hydroxymethyl)propane-1,3-diol and 1-(3,4-dihydroxyphenyl)-2 isopropylaminoethanol.

For pharmaceutical purposes, the particle size of the medicament powder should desirably be no greater than 100 micrometers diameter. In another embodiment, the particle size should be less than 25 micrometers in diameter. Desirably, the particle size of the finely-divided solid powder should for physiological reasons be less than about 25 micrometers and in other embodiments, less than about 10 micrometers in diameter.

Medicinal dispersions according the present invention contain a medicament dispersed in the dispersion in a therapeutically effective amount. "Therapeutically effective amount" means an amount sufficient to induce a therapeutic effect, such as bronchodilation or antiviral activity. The amount will vary according to factors know to those skilled in the art, such as pharmacological activity of the particular medicament, the condition being treated, the frequency of administration, the treatment site, and the presence of any other therapeutic agents or excipients being co-administered. The concentration of medicament depends upon the desired dosage but is generally in the range of 0.01 to 15, 0.01 to 10; 0.01 to 5; 0.01 to 4; 0.01 to 3; or 0.01 to 2 percent by weight and may be present in any amount or range between 0.001 and 15 percent by weight.

The medicinal dispersions of the invention may be delivered to the patient (mammal) by administration means including orally, injection (for example, IV, IP, IM, subQ), topical, through its nasal passage, by inhalation, and combinations thereof. Medicament delivery devices known to those skilled in the art may be used to administer the pharmaceutical dispersion. Such devices include for example, pump sprays, nebulizers, syringes, and the like.

Dispersion kits of the invention comprise organic nanoparticles and a dispersed phase component. The purpose of such a kit is to allow an end user of the dispersion to form the dispersion by adding a continuous phase, at a time the end user desires. The kit could contain pre-determined amounts of dispersed phase component and organic nanoparticles to be mixed with a suitable amount of a continuous phase. The dispersed phase component and the nanoparticles may be supplied as powders/particles, or pre-dispersed in a liquid medium. The nanoparticles and the dispersed phase component may be supplied in the kit mixed together or separately. The kit may also further comprise directions for use by the end user, for example, amounts, ratios, useful continuous phases, mixing steps, and the like, to form a dispersion of the invention.

The dispersions of the invention may also contain surface-modified inorganic nanoparticles in combination with organic nanoparticles. Surface-modified inorganic nanoparticles are described in U.S. application Ser. No. 10/449,359, filed on May 30, 2003, incorporated herein by reference for the description of surface-modified inorganic nanoparticles.

EXAMPLES

Surface Modified PAMAM G-2 Dendrimers (PAMAM G-2) Were Prepared as Follows:

Synthesis of Monofunctional Polyethylene Glycol (MPEG)-N-Hydroxysuccinimide Ester 100 grams (g) munofunctional polyethylene glycol (Polyglykol M, 1100 MW, available from Clariant, Sulzbach am Taunus, Germany, heretoafter referred to as MPEG 1100) was azeotropically dried in toluene for 24 hours followed by the addition of 2 molar excess of sodium metal (4.2 g) with constant stirring at 50° C. The temperature was increased to 75° C. and the reaction was allowed to proceed for the next 24 hours. The reaction was cooled to room temperature, any unreacted sodium removed, and further cooled to 10° C. t-butyl bromoacetate (30 mL, 2.25 molar excess, Aldrich Chemical Company) was added and the reaction was allowed to proceed for the next 48 hours with constant stirring, with the temperature gradually increasing to room temperature. The reaction was vacuum filtered to remove the NaBr salt, and the toluene was stripped off on the rotary-evaporator. The MPEG 1100 t-butyl ester product was dissolved in 300 mL methylene chloride and extracted with purified water (3×400 mL). The organic phase was dried with sodium sulfate, filtered, and the solvent was stripped off on the rotary-evaporator. Any residual volatiles were stripped by distillation at 110° C. under high vacuum. The product was hydrolyzed at 50° C. for 48 hours with 2.25 g of lithium hydroxide monohydrate in 175 mL of purified water. The reaction was acidified to pH3.0 with HCl and extracted with methylene chloride (4×300 mL). The organic phase was dried with sodium sulfate, filtered, and the solvent was stripped off on the rotary-evaporator to yield 12 g of MPEG 1100 acid which was dissolved in 150 mL tetrahydrofuran, a 2 molar excess of 2.6 g N-hydroxysuccinimide (Aldrich Chemical Company) was added, along with 2.6 g 1,3-dicyclohexylcarbodiimide (1.1 molar excess, Aldrich Chemical Company). The reaction was allowed to proceed at 0° C. for 24 hours with constant stirring. The resulting mixture was then vacuum filtered to remove the urea derived from 1,3-dicyclohexylcarbodiimide, followed by the removal of the THF on the rotary-evaporator.

Acetylated PAMAM G-2 MPEG 1100 Derivative 0.5 g PAMAM G-2 (Aldrich Chemical Company) was dissolved in 100 mL N,N-dimethylformamide at 0° C., and 5.4 g MPEG 1100-N-hydroxysuccinimide ester was added. The reaction was allowed to proceed with constant stirring for 2 hours.

Once warmed to room temperature, 100 mL toluene was added. The resulting solution was rinsed with purified water (5×300 mL) and 1.0 NaOH (5×200 mL). The toluene was stripped off on the rotary-evaporator, and the product was dried under high vacuum.

In order to cap off any terminal amino groups that had not reacted, the product was re-dissolved in 50 mL toluene and treated with excess acetic anhydride. Following 2 hours at 80° C., the solution was cooled slightly and 50 mL ethanol was added. All solvent was then stripped off on the rotary-evaporator, and the acetylated PAMAM G-2-MPEG 1100 derivative was dried under high vacuum.

Acetylated PAMAM G-2 MPEG 2000 Derivative

PAMAM G-2 MPEG 2000 derivative was prepared according to the same procedure used to make the acetylated PAMAM G-2 MPEG 1100 derivative described above except that 0.16 g PAMAM G-2 dendrimer (Aldrich Chemical Company) and 1.5 g MPEG 2000 succinimidyl propionate (MPEG-SPA, available from Nektar, San Carlos, Calif.) were used as the starting reagents.

Examples 1–4

Formulations of Albuterol Sulfate Stabilized in Ethanol by Acetylated PAMAM G-2 MPEG 1100 Derivative Formulations of stabilized dispersions were made by adding the amounts of the following ingredients listed in Table 1 below to a capped vial: the PAMAM G-2 MPEG 1100 derivative (described above), albuterol sulfate, HFA-134a fluorocarbon and 200 proof ethanol.

TABLE 1

Formulations of Albuterol Sulfate Stabilized by PAMAM G-2 MPEG 1100 Derivative

| Example | Acetlyated PAMAM G2 MPEG 1100 Derivative | Albuterol Sulfate | HFA-134a | Ethanol (200 proof) |
|---|---|---|---|---|
| 1 | 0.0257 g | 0.0385 g | 9.9626 g | 0 g |
| 2 | 0.0265 g | 0.0393 g | 8.9900 g | 1.0146 g |
| 3 | 0.0238 g | 0.0396 g | 9.9398 g | 0 g |
| 4 | 0.0251 g | 0.0389 g | 8.9585 g | 1.0104 g |

The sample vials with each formulation were shaken and then allowed to stand. The samples were rated as shown in Table 2 from 1–5 with 1 being no dispersion (clear solution with flocculated solid) and 5 being a totally dispersed system with uniform opacity. Examples 2 and 4 were given a 5 rating. Example 1 was rated a 3 and Example 3 was rated a 4.

TABLE 2

Visual Rating of Suspension Quality of Albuterol Sulfate Suspensions Stabilized by PAMAM G-2 MPEG 1100 Derivative

| Visual Rating of Suspension Quality | Description of Suspension |
|---|---|
| 1 | Agglomerates formed during shaking |
| 2 | Flocculation began immediately after shaking ceased |
| 3 | Flocculation began 1–5 seconds after shaking ceased |
| 4 | Flocculation began 5–30 seconds after shaking ceased |
| 5 | Flocculation began more than 30 seconds after shaking ceased |

Examples 5–6 Comparative Example A

Beclomethasone Dipropionate Dispersions in Water Stabilized by Acetylated PAMAM G-2 MPEG1100 Derivative Formulations of stabilized dispersions were made by adding the amounts of the following ingredients listed in Table 3 below to a capped vial: the acetylated PAMAM G-2 MPEG110 dendrimer derivative described above, beclomethasone dipropionate, and ultrapure (18 M$\Omega$)water.

TABLE 3

| Example | Acetylated PAMAM G-2 MPEG 1100 Derivative | Beclomethasone Dipopionate | Ultrapure Water |
|---|---|---|---|
| 5 | 0.0260 g | 0.0262 g | 10.0087 g |
| 6 | 0.0103 g | 0.0267 g | 10.0058 g |
| Comparative Example A | 0 g | 0.0255 g | 10.0245 g |

The sample vials with the formulations in Table 3 were shaken for about 30 seconds and then were allowed to stand undisturbed for 20 minutes. The suspension characteristics were observed. Comparative Example A had very little medicament dispersed within the liquid. The majority of the medicament particles remained on the surface of the liquid or on the walls of the vial above the liquid surface. Examples 5 and 6 had noticeably more medicament dispersed in the liquid and less medicament visible on the surface of the liquid or on the walls of the vial. Example 5 appeared to have more medicament dispersed in the liquid and less durg on the surface of the liquid and walls of the vial than did Example 6.

Examples 7 and 8 and Comparative Examples B and C

Stabilization of Dispersions of Budesonide and Fluticasone in Water using PAMAM G-2 MPEG 2000 Derivative Formulations of dispersions were made by adding the amounts of the ingredients listed in Table 4 to a capped vial.

TABLE 4

Formulations of Budesonide and Fluticasone Propionate in Water With PAMAM G-2 MPEG 2000 Derivative as Stabilizer

| Example | Acetylated PAMAM G-2 MEG 2000 Derivative | Budesonide | Fluticasone Propionate | Ultrapure (18 M$\Omega$) Water |
|---|---|---|---|---|
| 7 | 0.0052 g | 0.0159 g | 0.0000 g | 5.0231 g |
| Comparative Example B | 0.0000 g | 0.0180 g | 0.0000 g | 5.0256 g |
| 8 | 0.0053 g | 0.0000 g | 0.0122 g | 5.0000 g |
| Comparative Example C | 0.0000 g | 0.0000 g | 0.0144 g | 5.0742 g |

Each vial was shaken for 30 seconds. The vials were then left undisturbed for 20 minutes. After 20 minutes, the suspension characteristics of the vials were observed and recorded. Comparative Example B and Example 7 appeared uniformly dispersed initially after shaking. After 20 minutes, Comparative Example B had settled slightly, whereas Example 7 remained unchanged (no settling observed). Initially after shaking Comparative Example C and Example 8 appeared uniformly dispersed. After 20 minutes, the solid particulates in Comparative Example C had settled out whereas the solid particulates in Example 8 were still uniformly dispersed and indistinguishable from their appearance immediately after shaking.

Example 9

Stabilization of Dispersions of Carbon Black with Polystyrene Nanospheres 0.02 g 20 nm polystyrene nanospheres (Bang Laboratories, Inc., Fishers, Ind.) and 0.05 g carbon black were added to a capped small vial containing 0.93 g water. The vial was shaken by hand for 30 seconds. The vial was allowed to stand. After standing for 5 minutes, the dispersion was observed to be stable.

Examples 10 and 11

Stabilization of Carbon Black and Alumina with Octyl-Substituted $C_{60}$(octyl-$C_{60}$)

0.02 g octyl-$C_{60}$, 0.05 g carbon black, and 0.93 g toluene were added to a capped small vial. The vial was shaken by hand for 30 seconds. After standing for 5 minutes the dispersion was observed to be stable. A second vial was charged with 0.02 g octyl-$C_{60}$, 0.05 g alumina, and 0.93 g toluene. After shaking and standing for 5 minutes, this dispersion was also observed to be stable.

All patents, patent applications, and publications cited herein are each incorporated by reference, as if individually incorporated. Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A stable dispersion comprising:
   a continuous phase comprising a continuous liquid phase and a plurality of organic nanoparticles, wherein the nanoparticles are selected from the group consisting of branched or hyperbranched polyethylene oxide; and combinations thereof; and
   a dispersed phase comprising particles dispersed in the continuous phase.
2. The dispersion of claim 1 wherein the nanoparticles are surface-modified with polyethylene glycols or alkyl groups.
3. The dispersion of claim 2 wherein the alkyl groups are at least $C_3$.
4. The dispersion of claim 2 wherein the alkyl groups are not greater than $C_{30}$.
5. The dispersion of claim 2 wherein the alkyl groups range from $C_3$ to $C_{22}$.
6. The dispersion of claim 2 wherein the alkyl groups range from $C_3$ to $C_{18}$.
7. The dispersion of claim 2 wherein the alkyl groups range from $C_3$ to $C_{12}$.
8. The dispersion of claim 2 wherein the alkyl groups are $C_3$ to $C_8$ and any combination or integer therebetween.
9. The dispersion of claim 1 wherein the branched or hyperbranched polyethylene oxide nanoparticles comprise 4, 6, or 8 armed polyethylene oxide, or combinations thereof.
10. The dispersion of claim 1 wherein the continuous phase comprises an organic liquid.
11. The dispersion of claim 1 wherein said individual nanoparticles have a particle diameter no greater than about 50 nanometers.
12. The dispersion of claim 1 wherein said individual nanoparticles have a particle diameter in the range of from about 3 nanometers to about 50 nanometers.
13. The dispersion of claim 1 wherein said individual nanoparticles have a particle diameter of no greater than about 20 nanometers.
14. The dispersion of claim 1 wherein said individual nanoparticles have a particle diameter in the range of from about 3 nanometers to about 20 nanometers.
15. The dispersion of claim 1 wherein said individual nanoparticles have a particle diameter in the range of from about 3 nanometers to about 10 nanometers.
16. The dispersion of claim 1 wherein the dispersion comprises less than 0.001 percent by weight of surfactant, surface-active agents, detergents, and conventional dispersants.
17. The dispersion of claim 1 wherein the liquid continuous phase is selected from the group consisting of water, organic acids, alcohols, ketones, aldehydes, amines, amides, esters, glycols, ethers, hydrocarbons, halocarbons, monomers, oligomers, lubricating oils, vegetable oils, silicone oils, mineral and jojoba oils, fuel oils, kerosene, gasoline, diesel fuel, oligomers of ethylene glycol, alkyl and aryl nitro compounds, partially or fully fluorinated compounds, and combinations thereof.
18. The dispersion of claim 1 further comprising surface-modified inorganic nanoparticles.
19. A method of stabilizing a dispersion comprising adding an effective amount of organic nanoparticles to a dispersion comprising a dispersed solid phase and a liquid continuous phase, wherein the nanoparticles are selected from the group consisting of branched or hyperbranched polyethylene oxide; and combinations thereof.
20. A dispersion kit comprising a dispersed phase component to be dispersed in a continuous phase and organic nanoparticles selected from the group consisting of branched or hyperbranched polyethylene oxide and combinations thereof.
21. A stable dispersion comprising:
    a continuous phase comprising a continuous liquid phase and a plurality of organic nanoparticles that comprise polystyrene; and
    a dispersed phase comprising particles dispersed in the continuous phase wherein the particles are carbon black, titanium dioxide, pigments, abrasives, exfolients, or cosmetics.
22. A stable dispersion comprising:
    a continuous phase comprising a continuous liquid phase and a plurality of organic nanoparticles having an average particle diameter of less than 100 nanometers, wherein the nanoparticles are selected from the group consisting of amino acids, insoluble sugars and combinations thereof.
23. A method of stabilizing a dispersion comprising adding an effective amount of organic nanoparticles having an average particle diameter of less than 100 nanometers to a dispersion comprising a dispersed solid phase and a liquid continuous phase, wherein the nanoparticles are selected from the group consisting of insoluble sugars, amino acids and combinations thereof.
24. A dispersion kit comprising a dispersed phase component to be dispersed in a continuous phase and organic nanoparticles having an average particle diameter of less than 100 nanometers selected from the group consisting of insoluble sugars, amino acids, and combinations thereof.

* * * * *

UNITED STATES PATENT AND TRADEMARK OFFICE
CERTIFICATE OF CORRECTION

PATENT NO. : 7,109,247 B2
APPLICATION NO. : 10/449677
DATED : September 19, 2006
INVENTOR(S) : Jimmie R. Baran, Jr.

It is certified that error appears in the above-identified patent and that said Letters Patent is hereby corrected as shown below:

Title page,
Item (56), References Cited, U.S. PATENT DOCUMENTS, delete "6,586,483 B1" and insert in place there of -- 6,586,483 B2 --.
Item (56), References Cited, OTHER PUBLICATIONS, delete "Kibbe Ah et .," and insert in place thereof -- Kibbe Ah et al., --.

Column 3,
Line 36, delete "(G2–10)" and insert in place thereof -- (G2–G10) --.

Column 5,
Lines 15-16, delete "succinatc" and insert in place thereof -- succinate --.

Column 8,
Line 13, delete "munofunctional" and insert in place thereof -- monofunctional --.

Column 9,
Table 1, Line 27, delete "Acetlyated" and insert in place thereof -- Acetylated --.
Line 60, delete "5-6 Comparative" and insert in place thereof -- 5-6 and Comparative --.
Line 63, delete "MPEG1100" and insert in place thereof -- MPEG 1100 --.

Column 10,
Line 2, delete "MPEG110" and insert in place thereof -- MPEG 1100 --.
Line 3, delete "(18 MΩ)water" and insert in place thereof -- (18 MΩ) water --.
Line 25, delete "durg" and insert in place thereof -- drug --.

Signed and Sealed this

Tenth Day of April, 2007

JON W. DUDAS
*Director of the United States Patent and Trademark Office*